(12) United States Patent
Schlachte et al.

(10) Patent No.: US 10,978,881 B2
(45) Date of Patent: Apr. 13, 2021

(54) CHARGING APPARATUS AND METHOD

(71) Applicant: Ventiva, Inc., Milpitas, CA (US)

(72) Inventors: Carl P. Schlachte, Ben Lomond, CA (US); Rudy Vadillo, Gilroy, CA (US); Gary Alfred Oliverio, San Jose, CA (US)

(73) Assignee: Ventiva, Inc., Milpitas, CA (US)

( * ) Notice: Subject to any disclaimer, the term of this patent is extended or adjusted under 35 U.S.C. 154(b) by 510 days.

(21) Appl. No.: 15/673,060

(22) Filed: Aug. 9, 2017

(65) Prior Publication Data

US 2019/0052104 A1   Feb. 14, 2019
US 2020/0343752 A9   Oct. 29, 2020

Related U.S. Application Data

(60) Provisional application No. 62/491,515, filed on Apr. 28, 2017.

(51) Int. Cl.
| | |
|---|---|
| *H02J 7/00* | (2006.01) |
| *A61L 2/20* | (2006.01) |
| *H01T 23/00* | (2006.01) |
| H02J 7/02 | (2016.01) |
| H02J 50/10 | (2016.01) |
| H01M 10/44 | (2006.01) |
| H01M 10/60 | (2014.01) |

(52) U.S. Cl.
CPC ............... *H02J 7/00* (2013.01); *A61L 2/202* (2013.01); *H01T 23/00* (2013.01); *H02J 7/0044* (2013.01); *H01M 10/443* (2013.01); *H01M 10/60* (2015.04); *H02J 7/0091* (2013.01); *H02J 7/025* (2013.01); *H02J 50/10* (2016.02)

(58) Field of Classification Search
CPC ............................... H02J 7/0052; A61L 2/202
USPC ........................................................ 320/108
See application file for complete search history.

(56) References Cited

U.S. PATENT DOCUMENTS

| | | | | |
|---|---|---|---|---|
| 5,727,273 A | * | 3/1998 | Pai ......................... | A61C 17/16 15/22.1 |
| 8,481,970 B2 | * | 7/2013 | Cooper .................... | A61L 2/10 250/453.11 |
| 2003/0196687 A1 | * | 10/2003 | Campbell ................. | A61L 2/14 134/35 |
| 2004/0147293 A1 | * | 7/2004 | Park ........................ | H04M 1/04 455/573 |
| 2005/0168191 A1 | * | 8/2005 | Lee ........................ | G06F 1/1632 320/114 |

(Continued)

*Primary Examiner* — Jerry D Robbins
(74) *Attorney, Agent, or Firm* — Fenwick & West LLP

(57) ABSTRACT

A charging device includes a charging assembly for imparting a charge on a mobile device, a housing for receiving the mobile device to be charged, and for defining a cavity therein for housing the charging assembly. There is at least one air intake port in the housing for allowing air to be drawn into the cavity and at least one air exhaust port in the housing for allowing air to be exhausted from the cavity. There is an ionic wind generator, for generating an airstream to draw air into the housing through the at least one air intake port, through the cavity, and push air out of the housing through the at least one air exhaust port. The ionic wind generator comprises an emitter and a collector, such that when a voltage is applied to the emitter, air ionizes around the emitter and is drawn toward the collector, thereby creating the airstream.

20 Claims, 11 Drawing Sheets

(56) References Cited

U.S. PATENT DOCUMENTS

| | | | |
|---|---|---|---|
| 2006/0116159 A1* | 6/2006 | Lin | H04M 1/17 455/556.1 |
| 2010/0011613 A1* | 1/2010 | Husung | F26B 9/003 34/443 |
| 2012/0057356 A1* | 3/2012 | Hizer | F21V 29/63 362/373 |
| 2014/0375258 A1* | 12/2014 | Arkhipenkov | H02J 5/005 320/108 |
| 2015/0084591 A1* | 3/2015 | Kishima | H02J 7/0013 320/112 |
| 2015/0137747 A1* | 5/2015 | Salter | A61L 2/10 320/108 |
| 2016/0079840 A1* | 3/2016 | Tsoi | H02K 44/02 417/53 |
| 2016/0360644 A1* | 12/2016 | Bains | G06F 1/203 |

* cited by examiner

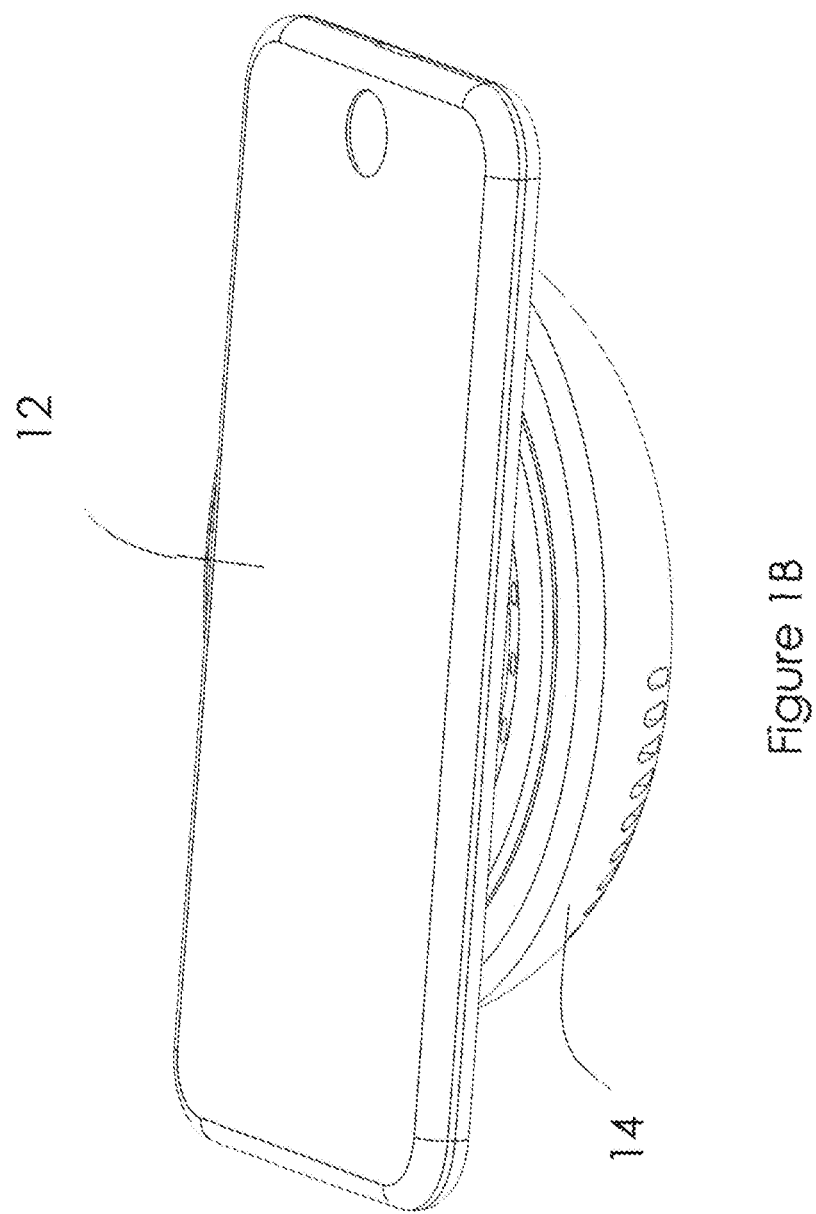

CHARGING APPARATUS AND METHOD

RELATED APPLICATIONS

This patent claims the benefit of U.S. Provisional Patent Application Ser. No. 62/491,515, filed on Apr. 28, 2017, the disclosure of which is hereby incorporated by reference in its entirety.

FIELD OF THE DISCLOSURE

This disclosure relates generally to wireless charging of mobile devices and, more particularly, to a charging apparatus and method for increased efficiency in charging using an ionic wind generator that also disinfects the mobile device as it charges.

BACKGROUND

Portable, or mobile electronic devices have become increasingly popular for a wide variety of activities. As such devices continue to be reduced in size to increase their portability, their functionality has been increased and, consequently, power demands also necessarily increase. As a result, batteries for these devices may need to be charged more frequently. However, many such devices, while being charged, can generate significant amounts of heat. Additionally, the charging devices also generate significant heat. Increased operating temperatures can degrade not only the performance of the devices and the length of a useable charge in these devices, but can also affect the time and quality of the charge imparted on a device. Therefore, it is advantageous to efficiently and effectively manage heat generated by these devices as they charge.

SUMMARY

In accordance with the present invention there is provided a charging device having a charging assembly to impart a charge on a mobile device, a housing for receiving a mobile device to be charged, and for defining a cavity therein for housing the charging assembly. There is also provided at least one air intake port in the housing for allowing air to be drawn into the cavity and at least one air exhaust port in the housing for allowing air to be exhausted from the cavity. There is further provided an ionic wind generator, for generating an airstream to draw air into the housing through the at least one air intake port, through the cavity, and pushing air out of the housing through the at least one air exhaust port. The ionic wind generator comprises an emitter and a collector, such that when a voltage is applied to the emitter, air ionizes around the emitter and is drawn to the collector, thereby creating the airstream.

In one embodiment, the charging device may have at least one rail for receiving a mobile device to be charged. The charging assembly may comprise an inductive coil for wirelessly imparting a charge on the mobile device. The exhaust port may be proximate to the rail for allowing air exhausted from the housing to be directed upon a surface of the mobile device being charged, and along a surface of the housing cooling the mobile device and the inductive coil. Alternatively, the air intake port may be proximate to the at least one rail to allow air being drawn into the housing to first be directed upon a surface of the mobile device and a surface of the housing to cool the mobile device and the inductive coil before being drawn into the housing. Once drawn into the housing, the airstream may provide additional cooling to the coil and other components located within the cavity of the housing. The charging device may further comprise one or more additional rails, wherein upon receiving a mobile device to be charged, the one rail, along with the one or more additional rails, form one or more channels between the mobile device and a surface of the housing whereby air from the at least one exhaust port, or alternatively the intake port, is directed along the surface of the mobile device and the surface of the housing, evenly distributing the air along the surfaces. Additionally, the surface of the housing proximate the rail may have a concaved shape. The at least one rail may further provide a stand-off distance between the mobile device being charged and an inductive coil to allow sufficient air flow to contact the surface of the mobile device being charged while also allowing the coil to couple with the mobile device allowing the coil to impart a charge on the battery of the mobile device while also cooling the mobile device, and or the coil. One or more of the rails may have at least one notch to provide a channel for directing exhausted air, or alternatively drawn in air, along a surface of the mobile device. The charging device may have additional rails for forming multiple channels between the mobile device and the surface of the housing for channeling cooling air along the mobile device, and along the surface of the housing to cool the mobile device and the inductive coil. The charging device may have a controller coupled to the charging assembly and the ionic wind generator, whereby the controller activates the ionic wind generator to create the airstream based on a monitored characteristic. The monitored characteristic may be an operational status of the charging device or the mobile device, a temperature threshold within the cavity, the presence of the mobile device, or a temperature of the mobile device.

In another embodiment, the charging assembly may include a pin connection for physically connecting to the mobile device in order to impart a charge on a battery of the mobile device, and the channel created by the at least one rail and the additional rail may be proximate to the exhaust port for directing air exhausted from the housing along the surface of the mobile device to cool the mobile device. Alternatively, the channel created by the at least one rail and any additional rails may be proximate to the air intake port, such that air drawn into the housing is first directed along a surface of the mobile device and a surface of the housing for cooling the mobile device. The at least one rail and any additional rails may further have at least one notch for providing one or more additional channels for directing exhausted air away from the surface of the mobile device and a surface of the housing, or alternatively, for directing drawn in air along the surface of the mobile device to be charged. The pin connection may be a USB connector or a Lightning connector.

There is also provided a method of charging a mobile device by creating an airstream within a housing of a charging device using an ionic wind generator, the housing having at least one air intake port and at least one air exhaust port, and a cavity there between formed by the housing, and a charging assembly located within the cavity for imparting a charge on a mobile device; drawing air into the housing using the airstream created by the ionic wind generator, whereby air drawn into the housing is carried through the cavity formed by the housing and across the charging assembly located within the cavity to cool the charging assembly; and exhausting air from the housing through the at least one exhaust port, the exhausted air being pushed from the housing by the airstream created by the ionic wind generator. The method may further include directing the exhausted air along a surface of the mobile device and a surface of the housing for cooling at least the mobile device. The method may further include monitoring a characteristic and creating the airstream in response to that monitored characteristic. The characteristic can be an operational status of the charging device or the mobile device, a temperature within the housing, the presence of a mobile device, or a temperature of the mobile device.

In still another embodiment, there is provided a disinfecting charging device having a charging assembly for imparting a charge on a mobile device. There is a housing, for receiving the mobile device to be charged, and for defining a cavity therein for housing the charging assembly. There is at least one air intake port in the housing for allowing air to be drawn into the cavity and at least one air exhaust port in the housing for allowing air to be exhausted from the cavity. There is an ionic wind generator, for generating an ozone airstream to draw air into the housing through the at least one air intake port, through the cavity, and push the ozone airstream out of the housing through the at least one air exhaust port. The ionic wind generator has an emitter and a collector such that when a voltage is applied to the emitter air ionizes at the emitter generating ozone which is drawn to the collector thereby creating the ozone airstream within the cavity. The at least one exhaust port is proximate to the mobile device allowing the ozone airstream exhausted from the housing to be directed upon a surface of the mobile device to disinfect the mobile device.

There is also provided a method of disinfecting a mobile device by generating an ozone airstream within the housing of a charging device using an ionic wind generator to generate ozone, the housing having at least one air intake port and at least one air exhaust port, and a cavity there between formed by the housing, and a charging assembly located within the cavity for imparting a charge on the mobile device; drawing air into the housing using the ozone airstream created by the ionic wind generator, whereby air drawn into the housing is carried through the cavity formed by the housing; exhausting the ozone airstream from the housing through the at least one exhaust port, the exhausted air being pushed from the housing by the ozone airstream created by the ionic wind generator; and directing the exhausted, ozone airstream along a surface of the mobile device disinfecting the device.

BRIEF DESCRIPTION OF THE DRAWINGS

The foregoing and other objects, features and advantages of embodiments of the present inventions will be apparent from the more particular description of preferred embodiments, as illustrated in the accompanying drawings in which like reference characters refer to the same elements throughout the different views in which:

FIGS. 1A and 1B are perspective views of a mobile device, and a horizontal charging device in accordance with an embodiment of the present invention;

DETAILED DESCRIPTION OF EMBODIMENTS

Figure 1A:
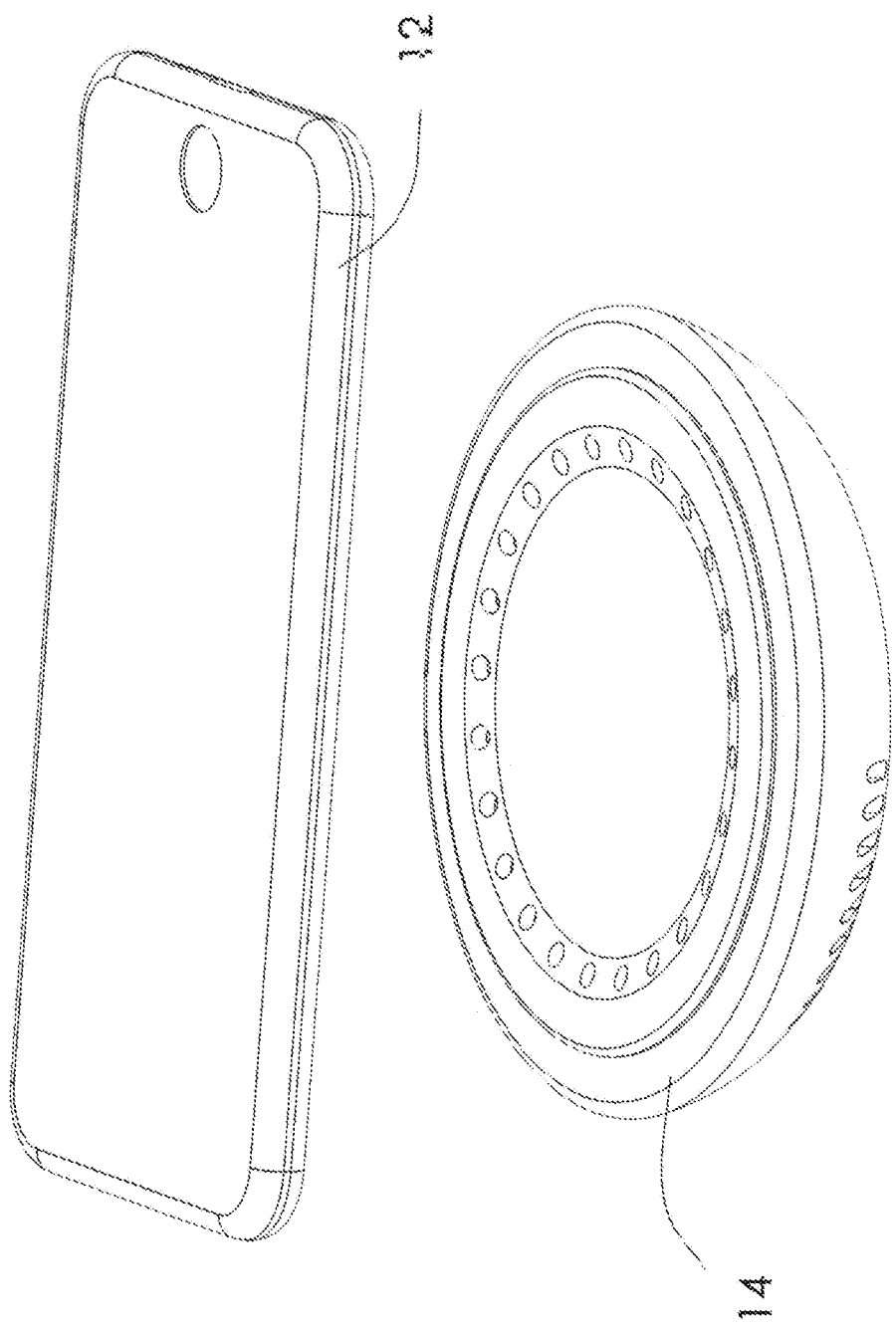

There is shown in FIGS. 1A and 1B a perspective view of a mobile device 12, and a horizontal charging device 14 according to one embodiment of the present invention. FIG. 1A shows mobile device 12 and charging device 14 separately, while FIG. 1B shows mobile device 12 placed on charging device 14 in a charging configuration.

Figure 2:
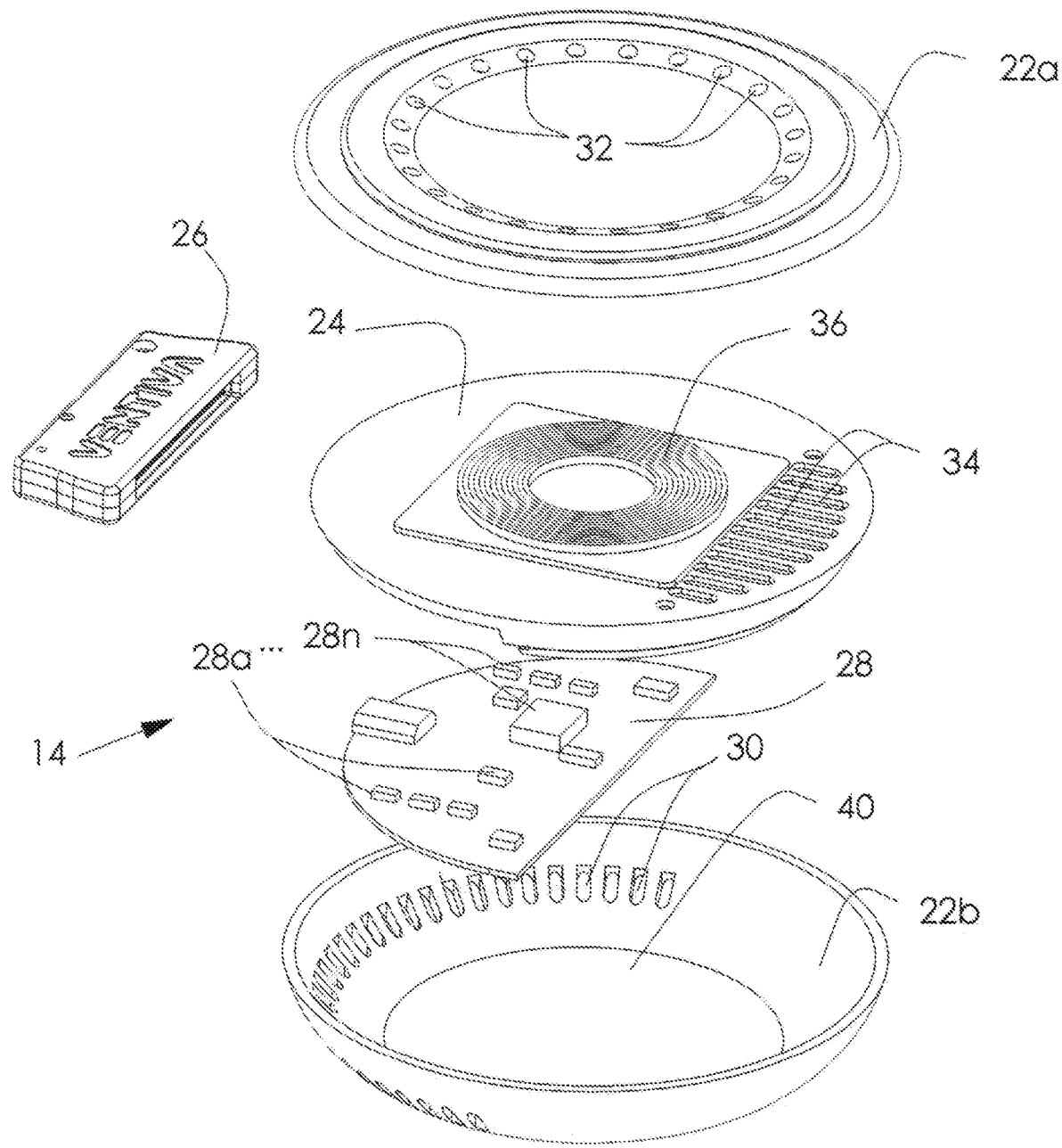
FIG. 2 is an exploded, perspective view of the horizontal charging device in accordance with an embodiment of the present invention.

FIG. 2 is an exploded, perspective view of charging device 14 according to one embodiment of the present invention. As shown in FIG. 2 there is provided an upper housing portion 22a and a lower housing portion 22b. As described in further detail below, upper and lower housing portions 22a, 22b form a charger housing 22 thereby defining at least one cavity 40 therein. Components of charging device 14 are housed within cavity 40. These components may comprise an inductive charging coil assembly 24, which inductively couples with a battery of mobile device 12 of FIGS. 1A and 1B, to impart a charge; an ionic wind generator or ionic air mover 26, which creates a cooling airstream without the need for a mechanical fan; and control board 28, which may comprise power, charging, cooling, high voltage, and other control components including one or more processors. Lower housing portion 22b may include one or more air intake ports 30 for drawing air into cavity 40 under the influence of air mover device 26 and upper housing portion 22a may include one or more air exhaust ports 32 for outputting air from cavity 40 and into contact with a surface of a mobile device placed on or near charging device 14 while charging. It should be noted that charging coil assembly 24 may further create first and second cavities as discussed further in reference to FIG. 3. It should also be noted that the orientation of air mover 26 may be reversed such that ports 30 become exhaust ports and ports 32 become intake ports in order to draw ambient air across a surface of mobile device 12 first, cooling it, and externally cooling charging assembly 24, then into cavity 40 to cool the charging components such as coil 36 and control circuit board 28 directly, and then exhausted through ports 30. Irrespective of the direction of the airstream created by air mover 26, by cooling the charging components within charger housing 22, and or the mobile device being charged, a battery of mobile device 12 can be charged more efficiently and quickly, while prolonging the life of charging device 14.

In one embodiment, charging assembly 24 comprises an inductive battery charging device that operates by wirelessly coupling with a coil assembly in mobile device 12 (not shown) when mobile device 12 is placed proximate to, or upon upper housing portion 22a of charging device 14, as shown in FIG. 1B, to deliver a charging current to the battery of mobile device 12. Charging assembly 24 comprises at least charging coil 36. Airflow vents 34 may be incorporated in charging assembly 24 in order to affect airflow across charging coil 36. Alternatively, air vents 34 may be created by a gap between charging assembly 24 and charger housing 22 when assembled, as would be readily apparent to one skilled in the art.

In a preferred embodiment, air mover device 26 is an ionic wind generation device that is located within cavity 40. Examples of ionic wind generation devices that may be utilized are the Ventiva ICE™ S1 device and the Ventiva ICE™ S2 device, both available from Ventiva, Inc. of Santa Clara, Calif. Air mover device 26 may include an intake portion for drawing air in and an exhaust portion for outputting the created airstream. Ionic wind generation devices comprise a collector and an emitter such that, when a voltage is applied to the emitter, air molecules are ionized around the emitter, which collide with other air molecules, moving them in the direction of the collector, thereby creating an air stream from a low pressure area around the emitter to a high pressure area around the collector, as will be discussed in detail with respect to FIGS. 5A and 5B. Moreover, as will be readily apparent to one skilled in the art, a preassembled ionic air mover as described above, while convenient, is not necessary, as discreet components as those shown and described in FIG. 5B may also be used.

In a preferred embodiment, control board 28 may include one or more microprocessors and associated hardware and software components for: monitoring temperature within cavity 40; creating a high voltage for powering the emitter of air mover 26; controlling the operation of air mover device 26 based on monitored characteristics such as a temperature threshold within cavity 40, the presence of, or level of charge of mobile device 12, or other characteristics that can be used to turn air mover device 26 on and off; monitoring power output of charging coil assembly 24; and other elements associated with the operation of charging device 14. Control board 28 may, for example, monitor and control the operation of both the charging coil assembly 24 and air mover device 26, or control board 28 may monitor and control air mover device 26 alone, while a second control board (not shown) monitors and controls charging coil assembly 24. Control board may also monitor the temperature of mobile device 12 to determine whether to turn air mover 26 on and off. If the temperature of mobile device 12 gets too hot, charging can be shut down, for example if the screen temperature exceeds 35 C, or the battery exceeds 42 C. Therefore, air mover device 26 may turn on at a threshold temperature below either of those temperatures to ensure those temperatures are not reached. Additionally, multiple control boards may be included for sharing, in a variety of configurations, the various monitoring and controlling functions associated with the operation of charging device 14. During operation, components of control board 28 generate heat within cavity 40 which must be dissipated. Moving the heated air away from the components and out of cavity 40 can prevent, or minimize adverse effects of the heat on the various components, while allowing charging coil 36 to charge a battery more efficiently.

Figure 3:
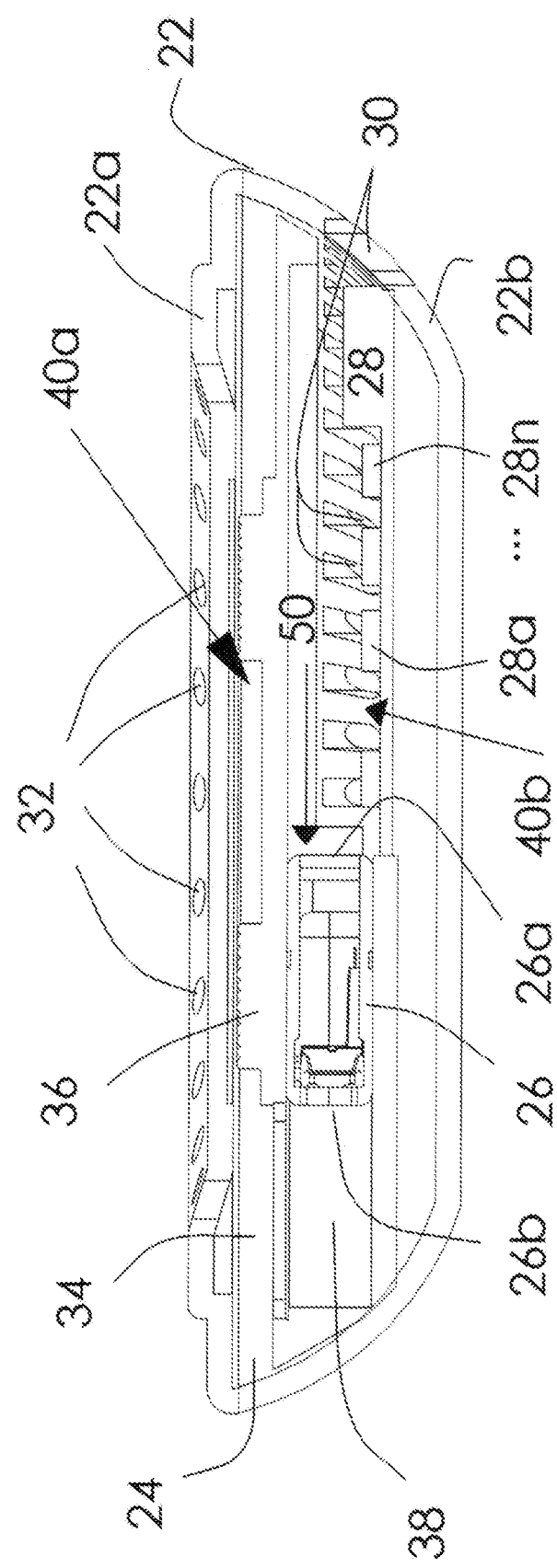
FIG. 3 is a cross-sectional view of the horizontal charging device in accordance with an embodiment of the present invention.

FIG. 3 is a cross-sectional view of charging device 14. As shown in FIG. 3 upper housing portion 22a having air exhaust ports 32, and lower housing portion 22b having air intake ports 30 are combined to form charger housing 22, and cavity 40 therein. Within cavity 40 are mounted charging assembly 24, air mover device 26 and control board 28. As previously discussed, charging assembly 24 may be mounted such that cavity 40 is divided into first and second cavities 40a and 40b. Also shown are airflow vents 34 incorporated into charging assembly 24, and charging coil 36. Alternatively, airflow vents could be created by an appropriately sized gap (not shown) created between charging assembly 24 and housing 22 such that the airstream generated by air mover 26 would pass from cavity 40b into cavity 40a.

As shown in FIG. 3 control board 28 may be placed within cavity 40 proximate to air intake ports 30, and between air intake ports 30 and air mover device 26. Air mover device 26 may be placed within cavity 40, and as shown within cavity 40b, between control board 28 and air vents 34, forming an air chamber 38 and drawing air across control board 28 to cool components mounted thereon. Air mover 26 may alternatively be placed anywhere along an airflow path 50, described in more detail with reference to FIG. 4.

FIG. 4 is a cross-sectional perspective view of charging device 14. Airflow path 50 of FIG. 3 is generally comprised of airstreams 50a through 50e. Air mover device 26 may be an ionic wind generation device that is located within cavity 40. An airstream is created by converting electrical energy into hydrodynamic energy. Thus, an air flow is created from intake portion 26a of air mover device 26 toward an exhaust portion 26b thereby developing an airflow through air mover 26 and thus cavity 40.

Figure 4A:
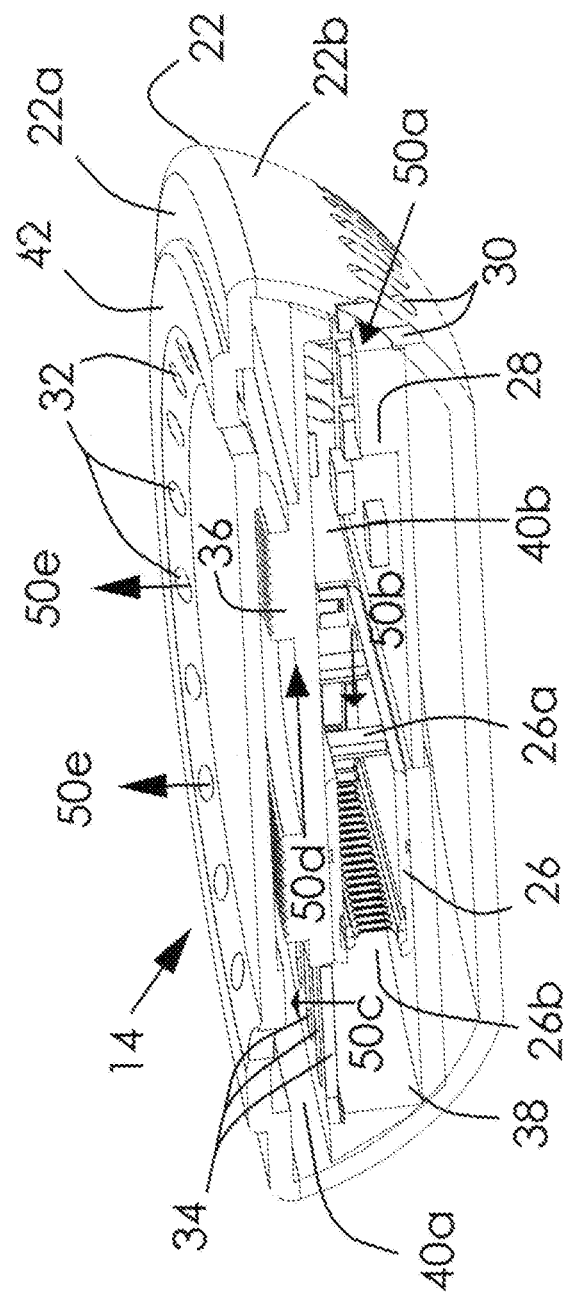
FIG. 4A is a perspective, cross-sectional view of the horizontal charging device in accordance with an embodiment of the present invention.

As shown in FIG. 4A, under the influence of air mover device 26, an ambient air stream 50a is drawn into cavity 40, as shown here, cavity 40b, through intake ports 30 of housing 22. As a result of ambient air stream 50a being pulled into cavity 40, an air stream 50b is drawn across components 28a-n of control board 28, to direct heated air away from the components. Air stream 50b enters air mover device 26 through intake portion 26a and exits through exhaust portion 26b. An air stream 50c, output from exhaust portion 26b, fills air chamber 38 resulting in an increase in air pressure within the air chamber. Air may slightly cool within chamber 38 and once air chamber 38 is pressurized, air flows through vents 34 into cavity 40a and an air stream 50d flows across charging assembly 24, and specifically charging coil 36, cooling the coil. Since the air within this portion of cavity 40a remains pressurized by the operation of air mover 26, an air stream 50e is forced from cavity 40a through exhaust ports 32.

The operation of the charging device 14, as described above, is effective in removing heat generated by the operation of the wireless charging device components, and in particular charging assembly 24 and charging coil 36. However, due to the proximity of a mobile device to exhaust ports 32 during charging, as shown in FIG. 1B, air stream 50e from ports 32 comes into contact with a surface of the mobile device, in particular the battery compartment where the charging battery generates heat, and effectively cools the mobile device by removing heat generated by the battery. Moreover, by efficiently cooling both the charging coil and the battery being charged, the battery may be charged quicker and more efficiently. The ability to inductively charge a mobile device is a function of the distance between the battery to be charged and charging coil 36. Accordingly, a ring, or circular rail 42 is provided that defines a standoff distance between mobile device 12 and charging coil 36. Thus, when a mobile device is place on rail 42, exhausted air stream 50e contacts a surface of the mobile device, then escapes along the edge portions of the mobile device that are not in contact with rail 42. Additional airflow may be provided by making the surface of housing portion 22a within rail 42 concave, as shown in FIG. 4A, thereby giving the airstream more room to circulate allowing the air to slightly cool before contacting the surface of the mobile device, providing even greater cooling.

Figure 4B:
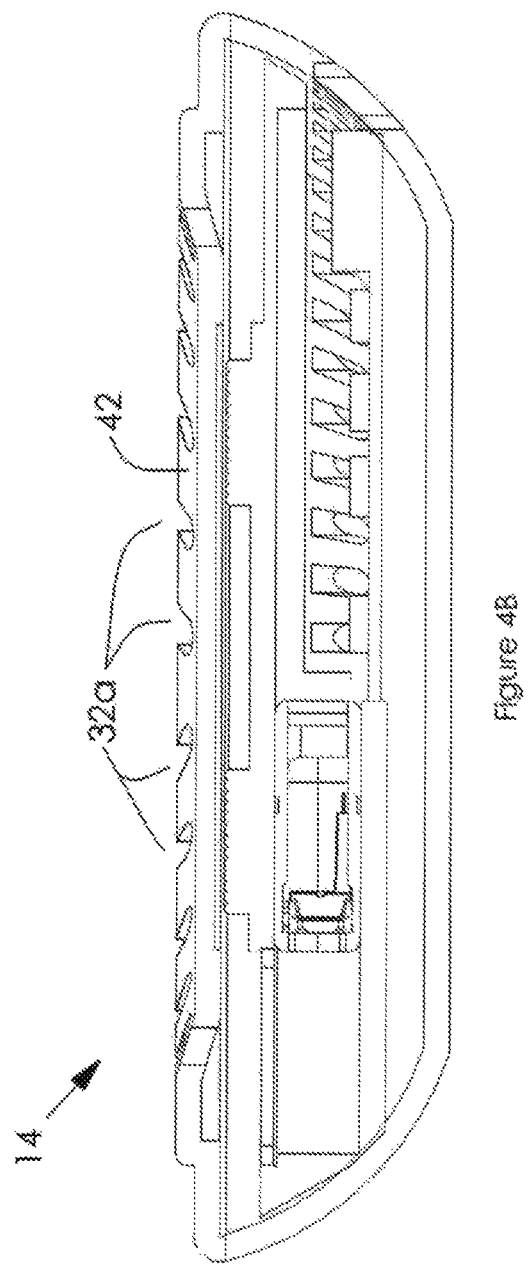
FIG. 4B is a cross-sectional view of the horizontal charging device in accordance with an embodiment of the present invention.

However, as the sizes of mobile devices vary, from larger cell phones to tablets, the mobile device may have dimensions greater than rail 42, thereby effectively sealing the top of charging device 14 and impeding, if not completely restricting, the ability of airstream 50e to flow past the mobile device, thereby restricting the ability of air to move through cavity 40, preventing cooling of the mobile device, and greatly limiting the cooling of charging components within housing 22. Accordingly, it may be advantageous to extend exhaust ports 32a horizontally and radially outward through rail 42, as shown in FIG. 4B, to create air flow channels that would still allow air to pass through and still allow an airflow to cool the charging components and the mobile device. Similarly, exhaust ports 32a could extend radially inward as well thereby creating a notched channel (not shown) that extends radially across the width of rail 42 to provide greater airflow from exhaust ports 32a as well as across a surface of a charging mobile device and into the concave surface of housing 22 to maximize cooling. While charging device 14 as shown is circular, this is for exemplary purposes only, and should not be considered a limitation of the invention. Similarly, ports 30 and 32 may be of varying shapes and sizes, and suited to allow sufficient airflow into and out of charging device 14.

Another feature of the present invention is that ionic wind generation devices, such as air mover 26, generate ozone during operation. Thus, airstreams 50c-50e at least partially comprise ozone, which is well known for having disinfecting properties. Mobile devices are in constant use and thus are constantly being touched, transferring bacteria to the device. In fact studies have shown that the surface of a typical mobile device can have more bacteria than a public toilet seat. Therefore, a further advantage of the present invention is the ability to disinfect a mobile device as it charges.

Figure 5A:
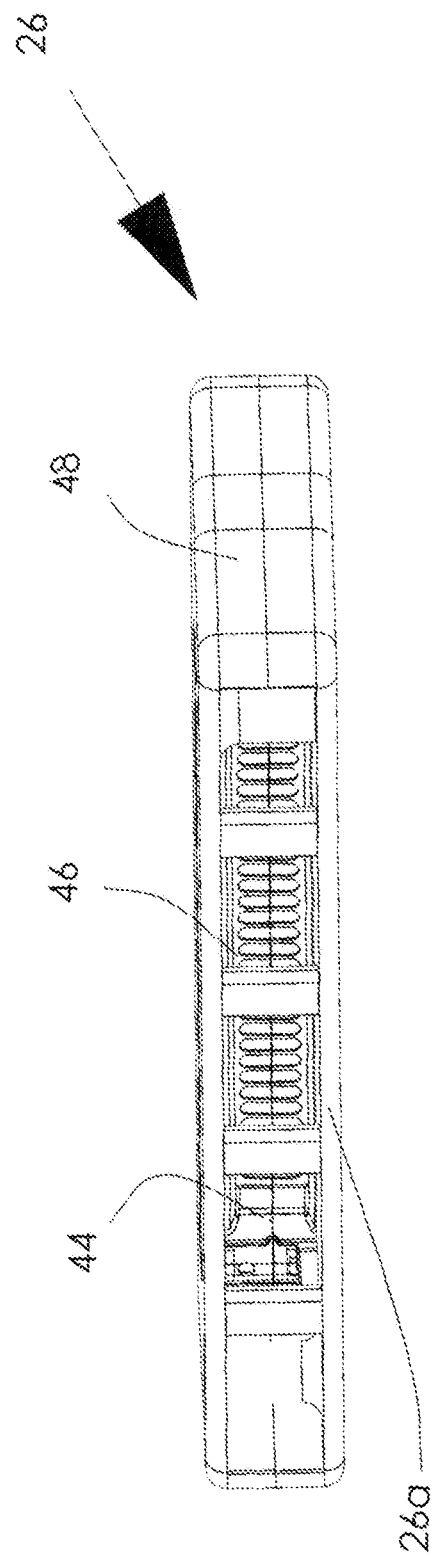
FIG. 5A is a perspective view of an ionic wind generator used in accordance with the present invention.
Figure 5B:
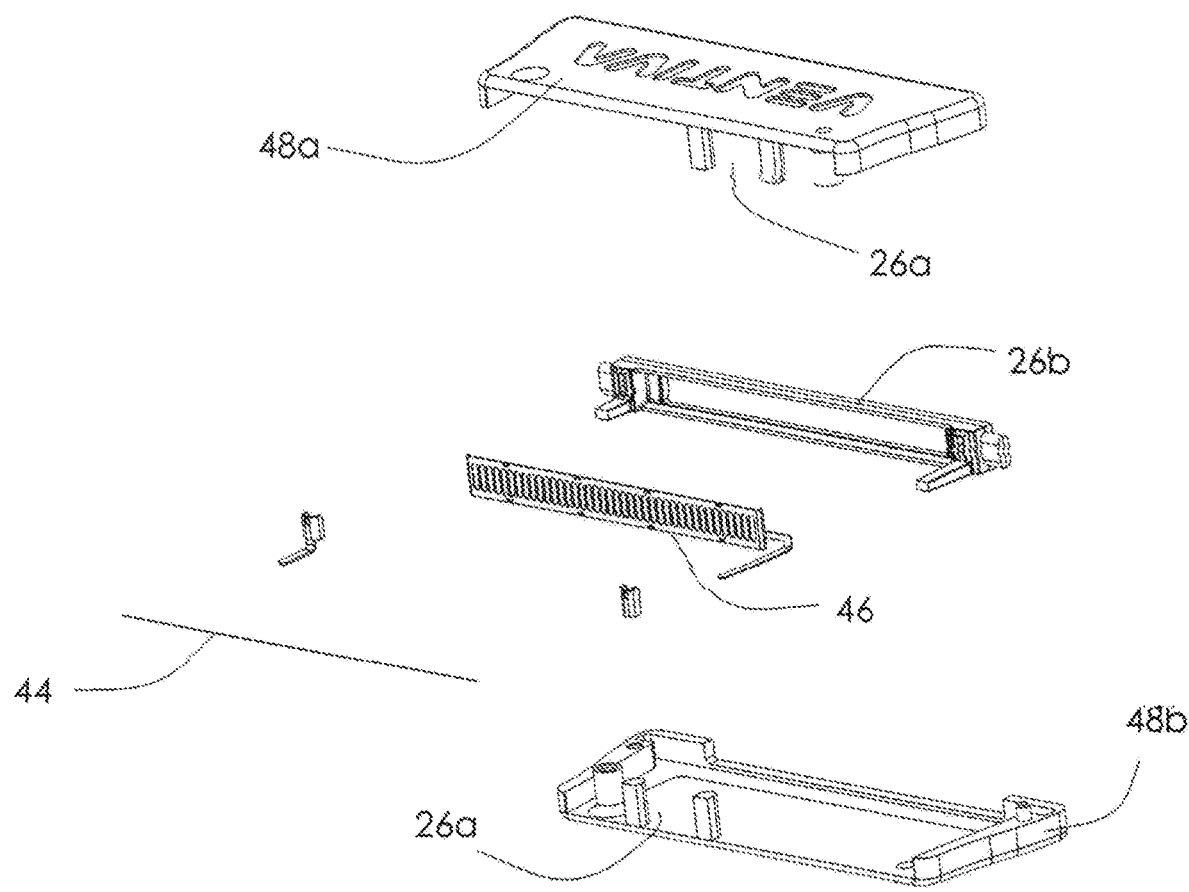
FIG. 5B is an exploded, perspective view of the ionic wind generator of FIG. 5A.

Turning to FIG. 5A, there is shown a perspective view of air mover device 26. Air mover device 26 is generally comprised of air intake portion 26a, and exhaust portion 26b, as previously discussed with respect to FIG. 4A, an emitter 44, which is located proximate to a collector 46, and air mover housing 48. FIG. 5B is an exploded perspective view of the air mover of FIG. 5A. Air intake portion 26a is formed when air mover housings 48a and 48b are combined to form air mover housing 48. Referring back to FIG. 5A, when a high voltage from control board 28 of FIG. 4A is applied to emitter 44, air near emitter 44 is ionized. The ionized air is drawn to collector 46. As the ionized air moves towards collector 46 it collides with other air molecules, causing further ionization of some additional air molecules, causing additional collisions, all of which continue to be drawn to collector 46, pushing other air molecules in the same direction. The result is a low pressure area near emitter 44 and a high pressure area near collector 46. This culminates in the creation of an air stream, as previously discussed, from intake port 26a through exhaust portions 26b, which draws air into ports 30, through cavity 40b and pushes air out through cavity 40a to exhaust ports 32, as previously discussed with respect to FIG. 4A.

Figure 6:
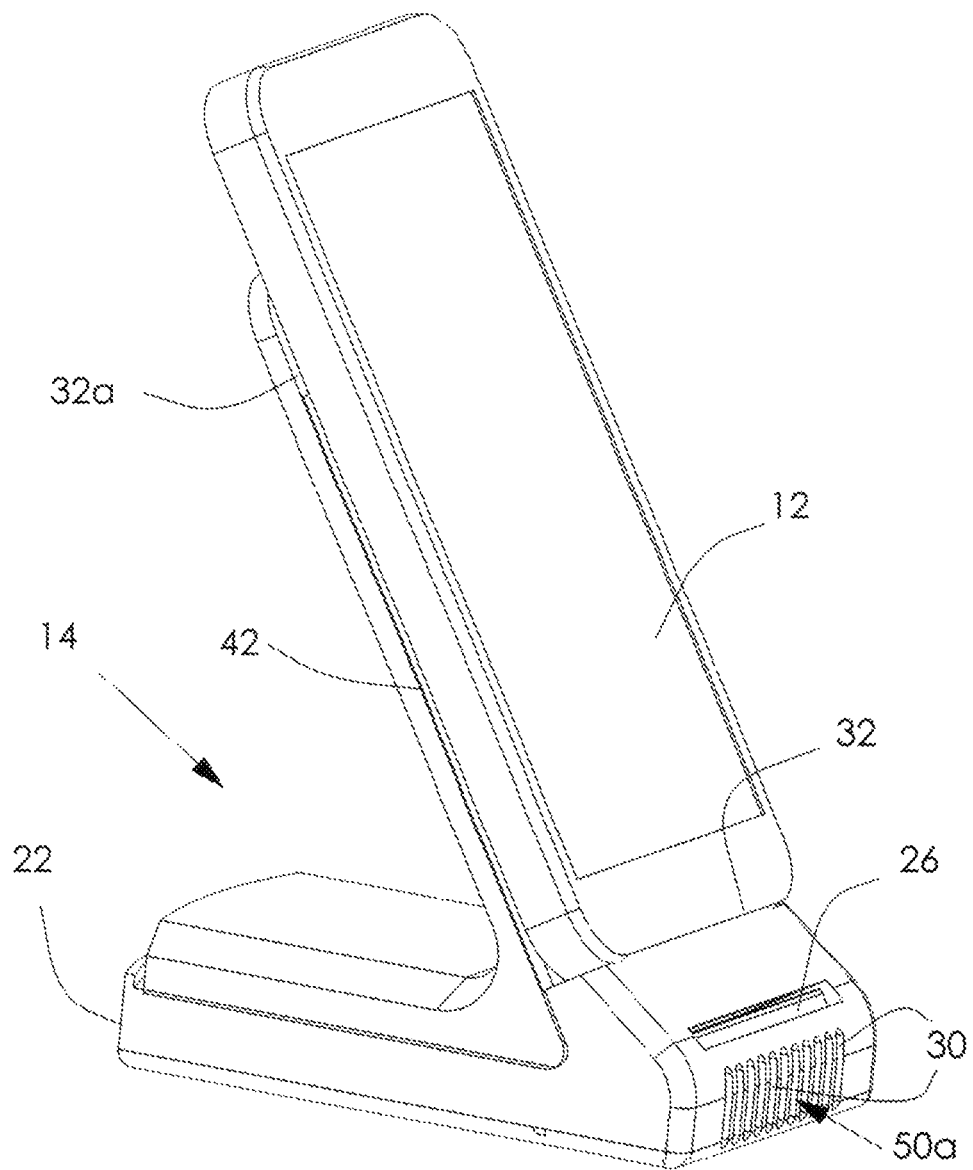
FIG. 6 is a perspective view of a mobile device, and a vertical charging device in accordance with an embodiment of the present invention.
Figure 7:
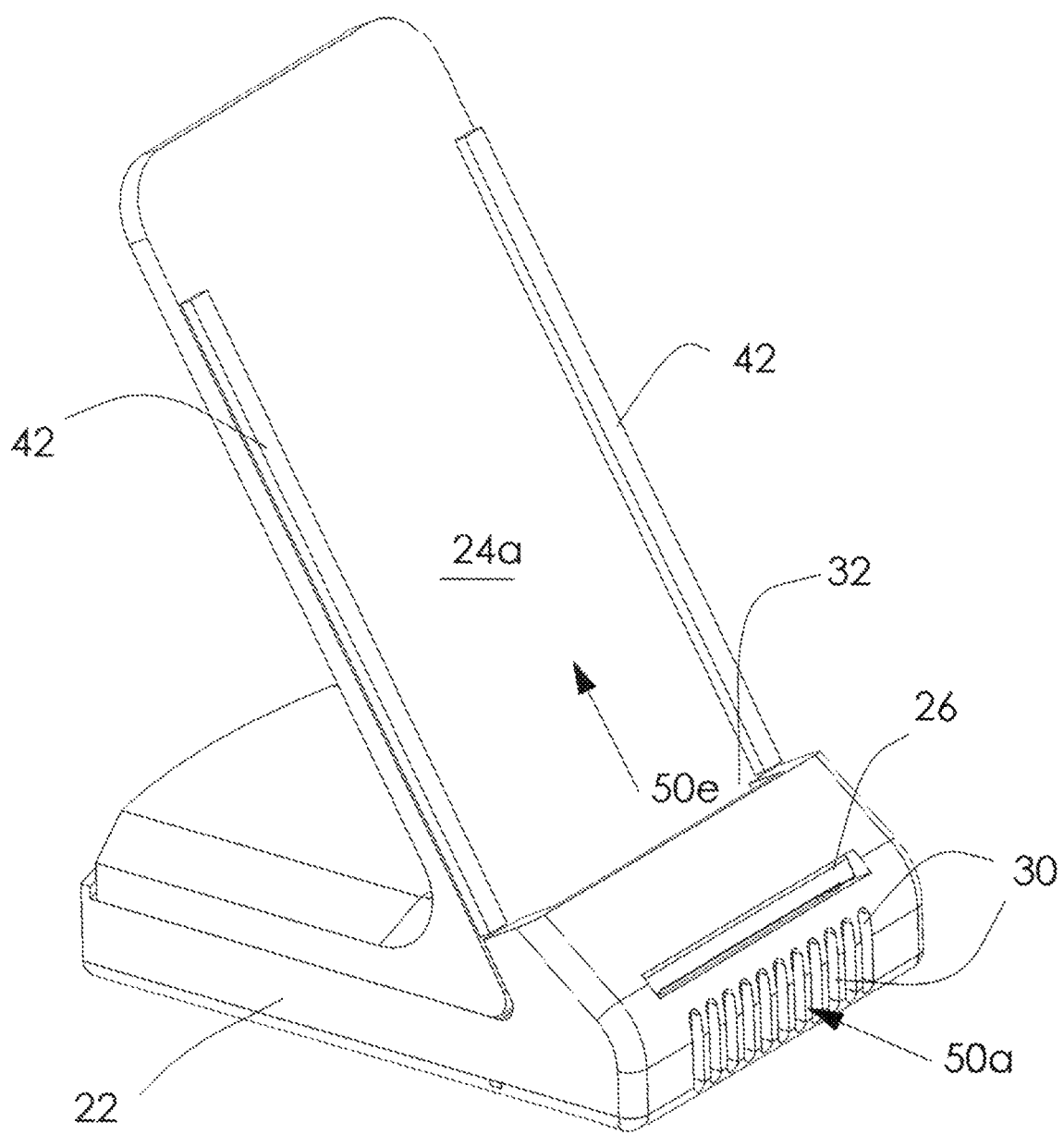
FIG. 7 is a perspective view of the vertical charging device in accordance with an embodiment of the present invention.

There is shown in FIG. 6 another embodiment of the present invention. Vertical charging device 14 allows a user to easily view, and or use mobile device 12 as it charges. The vertical charging device of FIG. 6 charges and cools in a manner similar to that described in FIGS. 1-4. However, charging may be done through an inductive coil, as previously described, as well as through conventional charging techniques using a transformer and various pin connectors such as USB, micro USB, Apple® Lightning, and other pin connectors well known in the art. An air mover device 26, as described in FIG. 5A, creates an air stream that draws air into one or more air intake ports 30 through a cavity 40 (not shown) within housing 22 and exhausts air through an exhaust port 32. At least 2 rails 42 form a channel 32a when mobile device 12 is placed on charging device 14. FIG. 7 shows a perspective view of charging device 14 without a mobile device. As can be seen, exhaust port 32 expels airstream 50e. Rails 42 provide a dual function. The height of rails 42 create the standoff distance between a battery of mobile device 12 of FIG. 6, similar to rail 42 of FIG. 4A, while also creating a channel when a mobile device is placed on rails 42 to be charged. This channel forces airstream 50e along a charging surface 24a (behind which is a charging assembly and charging coil similar to that described in FIGS. 1-4) as well as a surface of mobile device 12, namely the battery compartment housing battery 52 (see FIG. 8), thereby externally cooling the charging coil and the mobile device simultaneously. In the embodiment where charging is done through conventional USB connectors and the like, airstream 50e is used only to cool mobile device 12. Cooling of the charging assembly is accomplished via intake port 30a and airstream 50b as discussed in reference to FIG. 8.

Figure 8:
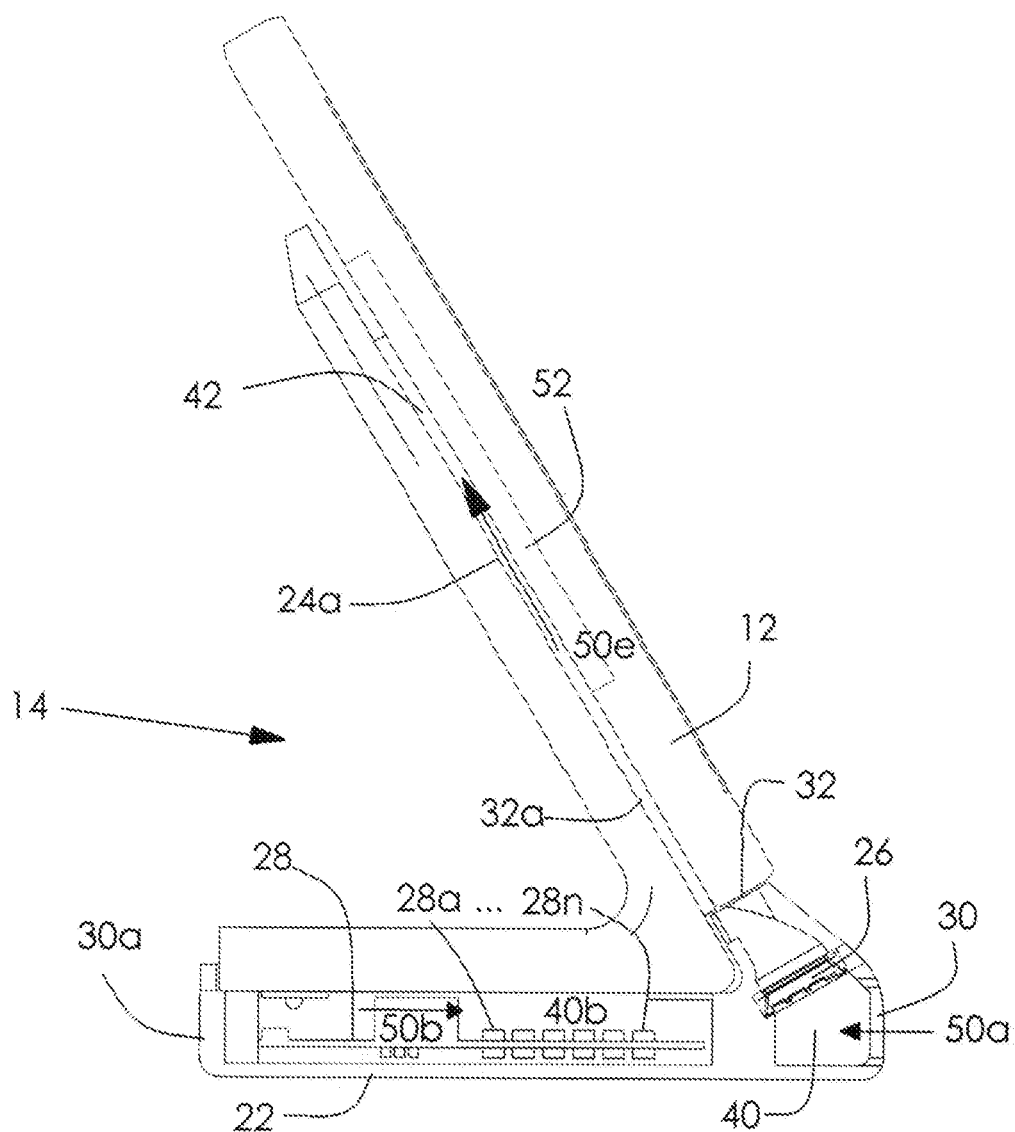
FIG. 8 is a perspective, cross-sectional view of a mobile device and the vertical charging device in accordance with an embodiment of the present invention.

Turning to FIG. 8, there is shown a cross-sectional, perspective view of vertical charging device 14. As can be seen air mover 26, comprising collector 46 and emitter 44 of FIG. 5B, creates an airstream that draws airstream 50a through intake port 30 into cavity 40 when a high voltage from control board 28 is applied to the emitter, as previously discussed. The resulting airstream is pushed out exhaust port 32 and through a channel 32a formed by mobile device 12, charging device 14 and rails 42, thereby cooling both battery 52 and charging coil 36 of charging assembly 24, as the airstream passes across charging area 24a. Channel 32a must be of sufficient height, defined by rails 42, to allow coil 36 to couple with mobile device 12 and charge battery 52 while still providing adequate airflow through the channel to cool both coil 36 and battery 52. In order to increase airflow, channels similar to those discussed with respect to rail 42 of FIG. 4A, may be notched in rails 42 of FIG. 7 to provide additional airflow paths. In yet another embodiment, multiple rails 42 may be provided across and along the charging area, creating multiple channels 32a to more evenly distribute airstream 50e along charging area 24a and battery 52. Additionally, while not shown, exhaust port 32 may sufficiently widen such that the exhausted airstream containing ozone, is also directed along both sides of the mobile device to both cool and disinfect the mobile device. As will be readily apparent to one skilled in the art, various combinations of rails and notches may be used to effectively cool mobile device 12 and charging area 24a, while maximizing coupling of the coil and mobile device.

In yet another embodiment air intake port 30a may be placed at the rear of charging device 14, instead of the front, such that airstream 50b created by air mover 26 is drawn into cavity 40b and across components 28a-n to cool them in a manner similar to that discussed with reference to FIG. 4, before being exhausted through port 32.

While the present disclosure uses the example of a mobile device battery being charged in conjunction with charging device 14, it will be understood that any portable device capable of being charged may be used in conjunction with charging device 14 to obtain the benefits described herein. For example, laptop computers, tablets, virtual reality headsets, smart watches and similar devices would benefit from the heat-removing and disinfectant features provided by the disclosed apparatus and method.

Having thus described several aspects of various embodiments of the present invention, it is to be appreciated various alterations, modifications, and improvements will readily occur to those skilled in the art without diverging from the scope of the present invention. Such alterations, modifications, and improvements are intended to be part of this disclosure, and are intended to be within the spirit and scope of the inventions. Accordingly, the foregoing description and drawings are by way of example only.

What is claimed is:

1. A charging device comprising:
    a charging assembly for imparting a charge on a mobile device, wherein said charging assembly comprises an inductive coil for wirelessly imparting the charge on the mobile device to be charged;
    a housing, for receiving the mobile device to be charged, and for defining a cavity therein for housing the charging assembly, the housing having a surface of the housing adapted for placement of the mobile device on the housing;
    at least one air intake port in the housing for allowing air to be drawn into the cavity;
    at least one air exhaust port in the housing for allowing air to be exhausted from the cavity and directed over a surface of the mobile device;
    a continuous airflow path connecting the at least one air intake port with the at least one air exhaust port;
    at least one rail for receiving the mobile device to be charged, wherein the at least one rail provides a stand-off distance between the mobile device to be charged and the inductive coil, wherein the stand-off distance is small enough to allow the inductive coil to impart a charge on a battery of the mobile device and the stand-off distance is also sized to allow an airstream sufficient to cool internal components of the mobile device and to cool the inductive coil; and
    an ionic wind generator, for generating the airstream by drawing air into the housing through the at least one air intake port, through the cavity, and pushing air out of the housing through the at least one air exhaust port, the ionic wind generator comprising an emitter and a collector that are oriented substantially perpendicular to each other, wherein a voltage applied to the emitter ionizes air at the emitter which is drawn to the collector thereby creating the airstream within the cavity and over the surface of the mobile device to cool internal components of the mobile device.

2. The charging device of claim 1, wherein the at least one exhaust port is proximate to the at least one rail for allowing air exhausted from the housing to be directed upon the surface of the mobile device to be charged and the surface of the housing, for at least cooling at least the mobile device.

3. The charging device of claim 2, further comprising at least one additional rail, wherein the at least one rail and the at least one additional rail, upon receiving the mobile device to be charged, form at least one channel with the mobile device to be charged whereby air from the at least one exhaust port is directed along the surface of the mobile device to be charged and the surface of the housing for cooling the mobile device and the inductive coil.

4. The charging device of claim 3, wherein at least one of the at least one rail and the at least one additional rail further comprises at least one notch for providing a channel for directing air away from the surface of the mobile device to be charged and the surface of the housing for cooling the mobile device and the inductive coil.

5. The charging device of claim 1, wherein the at least one air intake port is proximate to the at least one rail for allowing air drawn into the housing to first be directed upon the surface of the mobile device to be charged and the surface of the housing for cooling at least the mobile device.

6. The charging device of claim 5, further comprising at least one additional rail, wherein the at least one rail and the at least one additional rail, upon receiving the mobile device to be charged, form at least one channel with the mobile device to be charged whereby air drawn into the at least one air intake port is first directed along the surface of the mobile device to be charged and the surface of the housing for cooling the mobile device and the inductive coil.

7. The charging device of claim 6, wherein at least one of the at least one rail and the at least one additional rail further comprises at least one notch for providing a channel for first directing air along the surface of the mobile device to be charged and the surface of the housing for cooling the mobile device and the inductive coil.

8. The charging device of claim 1, wherein the surface of the housing proximate the rail is concave.

9. The charging device of claim 1, wherein the at least one rail further comprises at least one notch for providing a channel for directing air away from the surface of the mobile device to be charged and the surface of the housing for cooling at least the mobile device.

10. The charging device of claim 1, wherein the airstream within the cavity is drawn across the charging assembly to cool the inductive coil, before being exhausted from the housing through the at least one exhaust port.

11. The charging device of claim 1, further comprising at least one additional rail, wherein the at least one rail and the at least one additional rail, upon receiving the mobile device to be charged, form at least one channel with the mobile device to be charged and the surface of the housing for cooling the mobile device.

12. The charging device of claim 11, wherein the channel created by the at least one rail and the at least one additional rail is proximate to the at least one exhaust port, for directing air exhausted from the housing along the surface of the mobile device to be charged and the surface of the housing for cooling the mobile device.

13. The charging device of claim 12, wherein at least one of the at least one rail and the at least one additional rail further comprises at least one notch for providing a channel for directing air away from the surface of the mobile device to be charged and the surface of the housing for cooling the mobile device.

14. The charging device of claim 11, wherein the channel created by the at least one rail and the at least one additional rail is proximate to the at least one air intake port, for directing air drawn into the housing to be first directed along the surface of the mobile device to be charged and the surface of the housing for cooling the mobile device.

15. The charging device of claim 14, wherein at least one of the at least one rail and the at least one additional rail further comprises at least one notch for providing a channel for directing air along the surface of the mobile device to be charged and the surface of the housing for cooling the mobile device.

16. The charging device of claim 11, wherein the airstream within the cavity is drawn across the charging assembly to cool the charging assembly, before being exhausted from the housing through the at least one exhaust port.

17. The charging device of claim 1, further comprising a controller coupled to the charging assembly and the ionic wind generator, wherein the controller activates the ionic wind generator based on a monitored characteristic.

18. The charging device of claim 17, wherein the monitored characteristic is the presence of a mobile device status.

19. The charging device of claim 17, wherein the monitored characteristic is a temperature threshold within the cavity.

20. The charging device of claim 17, wherein the monitored characteristic is a temperature threshold of the mobile device.

\* \* \* \* \*